US012807604B2

(12) United States Patent
Donavalli et al.

(10) Patent No.: US 12,807,604 B2
(45) Date of Patent: Nov. 24, 2026

(54) METHODS OF MAKING HARMINE DERIVATIVE ADDUCTS AND DIMERS

(71) Applicant: Ankh Life Sciences Limited, Dublin (IE)

(72) Inventors: Krishna Mohan Donavalli, Sterling, KS (US); Rajni Verma, Sterling, KS (US); Gene H. Zaid, Hutchinson, KS (US)

(73) Assignee: Ankh Life Sciences Limited, Dublin (IE)

(*) Notice: Subject to any disclaimer, the term of this patent is extended or adjusted under 35 U.S.C. 154(b) by 391 days.

(21) Appl. No.: 18/458,604

(22) Filed: Aug. 30, 2023

(65) Prior Publication Data

US 2024/0092780 A1 Mar. 21, 2024

Related U.S. Application Data

(60) Provisional application No. 63/405,163, filed on Sep. 9, 2022, provisional application No. 63/402,321, filed on Aug. 30, 2022.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 3,413,293 | A | 11/1968 | Schut | |
| 4,218,448 | A | 8/1980 | Aldrich et al. | |
| 10,947,253 | B2 * | 3/2021 | Blagg | C07D 215/06 |
| 11,576,902 | B2 * | 2/2023 | Zaid | A61P 31/14 |
| 12,129,265 | B2 * | 10/2024 | Zaid | A61P 35/00 |
| 2024/0002405 | A1 * | 1/2024 | Verma | C07D 519/00 |

FOREIGN PATENT DOCUMENTS

| | | |
|---|---|---|
| CN | 111675725 | 9/2020 |

OTHER PUBLICATIONS

Jiang et. al. "Cytotoxic Bis-3,4-dihydro-b-carbolines and Bis-b-carbolines" Journal of Enzyme Inhibition and Medicinal Chemistry, 2002, 17, 6, 369-374. DOI: 10.1080/14756302100005631. (Year: 2002).*

(Continued)

*Primary Examiner* — Jennifer A Berrios
*Assistant Examiner* — Sophia Reilly
(74) *Attorney, Agent, or Firm* — Hovey Williams LLP; Crissa A. Cook

(57) ABSTRACT

The present disclosure is concerned with β-carboline adducts and dimer compounds comprising two β-carboline moieties and methods of synthesizing the same. The methods described herein may also be used to synthesize a wide array of β-carboline adducts and dimer compounds, depending upon the reactants used. Generally, the method comprises reacting a tryptamine and an acid chloride or diacid chloride in acetonitrile to yield harmaline compounds which can be easily converted to harmine or tetrahydroharmine if desired.

15 Claims, 8 Drawing Sheets

(56) References Cited

OTHER PUBLICATIONS

Yu et. al. "Unusual role of labile phenolics in imparting flame resistance to polyamide" Polymer Degradation and Stability, 2020, 175, 109103. DOI: 10.1016/j.polymdegradstab.2020.109103. (Year: 2020).*

Hayashi et. al. "Pot economy and one-pot synthesis" Chem. Sci. 2016, 7, 866. DOI: 0.1039/c5sc02913a (Year: 2016).*

Remington's Pharmaceutical Sciences (21st Ed) New York, NY: Lippincott Williams and Wilkins 2005. Select pages. (Year: 2005).*

Dunetz et. al. "Large-Scale Applications of Amide Coupling Reagents for the Synthesis of Pharmaceuticals" Org. Process Res. Dev. 2016, 20, 140-177. DOI: 10.1021/op500305s (Year: 2016).*

International Search Report and Written Opinion in corresponding PCT/US2023/073139, dated Jan. 23, 2024.

Alehashem, et al., "The synthesis of some novel stilbene dimers incorporating diamide tethers: studies in single electron transfer oxidation (FeCl3)", RSC Adv., 2018, 8(5), 2506-2520.

* cited by examiner

Harmaline dimer

Tetrahydro Harmine dimer

Harmaline dimer

Harmine dimer 6-methoxy tryptamine

GZ440/6

*Initial Reaction – GK Synthesis Mechanism*

*Subsequent Reaction – GK Synthesis Mechanism*

6-methoxy tryptamine 3-cyclobutylpropanoyl chloride

GK282

Chemical Formula: $C_{18}H_{22}N_2O$
Exact Mass: 282.17

6-methoxy tryptamine succinyl chloride

GK426

METHODS OF MAKING HARMINE DERIVATIVE ADDUCTS AND DIMERS

CROSS-REFERENCE TO RELATED APPLICATIONS

The present application claims the priority benefit of U.S. Provisional Patent Application Ser. No. 63/402,321, filed Aug. 30, 2022, entitled DIMER COMPOUNDS SYNTHESIZED USING GK METHOD, and U.S. Provisional Patent Application Ser. No. 63/405,163, filed Sep. 9, 2022, each of which is incorporated by reference in its entirety herein.

BACKGROUND OF THE INVENTION

Field of the Invention

The present disclosure is broadly concerned with β-carboline adducts and novel dimer compounds comprising two β-carboline moieties and novel methods of synthesizing the same. The novel methods described herein may also be used to synthesize a wide array of adducts and dimer compounds, depending upon the reactants used.

Description of Related Art

β-Carboline (9H-pyrido[3,4-b]indole) represents the basic chemical structure for more than one hundred alkaloids and synthetic compounds. The effects of these substances depend on their respective substituents, and they have been shown to have a variety of therapeutic properties. Examples of various β-carbolines and derivatives are shown below.

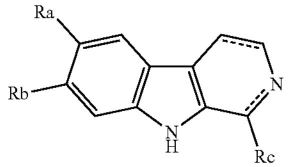

| Short Name | Ra | Rb | Rc | Structure |
|---|---|---|---|---|
| β-Carboline | H | H | H | 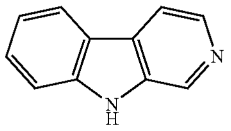 |
| Pinoline | $OCH_3$ | H | H | 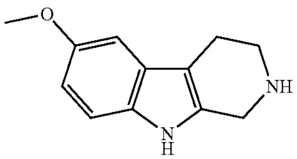 |
| Harmane | H | H | $CH_3$ | 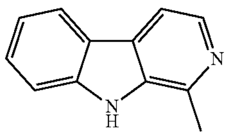 |
| Harmine | H | $OCH_3$ | $CH_3$ | 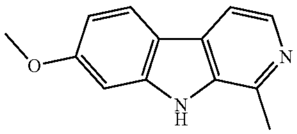 |
| Harmaline | H | $OCH_3$ | $CH_3$ | 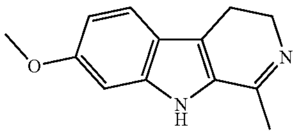 |
| Harmalol | H | OH | $CH_3$ | 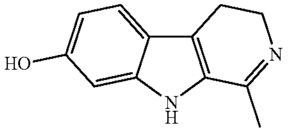 |

-continued

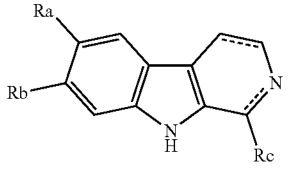

| Short Name | Ra | Rb | Rc | Structure |
|---|---|---|---|---|
| Tetrahydroharmine | H | $OCH_3$ | $CH_3$ | 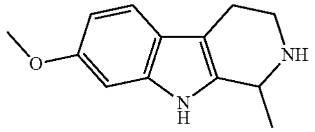 |
| 9-Methyl-β-carboline* | H | H | H | 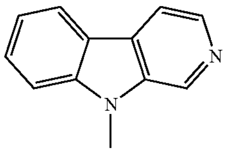 |
| 3-Carboxy-Tetrahydrononharman | H | H | H/$CH_3$/COOH | 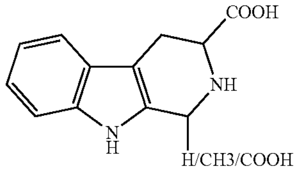 |

*with methyl on indole nitrogen

β-carbolines and derivatives (such as harmine, harmaline), including dimers thereof can be synthesized various ways. The traditional methods for β-carboline synthesis involve at least two separate steps as shown in FIG. 1A. There are also several ways to synthesize harmaline dimer compounds, yet each have their drawbacks. For example, the traditional harmaline+aldehyde reaction is limited to only those aldehydes that react with harmaline. This limits the tether length between the compounds and substitution options at the tether. Furthermore, the traditional method used to synthesize harmaline dimer molecules involves two independent steps, as shown in FIG. 1B.

In a first step, dicarboxylic acid is reacted with tryptamine in presence of reagents, such as 1-Ethyl-3-(3-dimethylaminopropyl)carbodiimide (EDC) and N,N'-Dicyclohexylcarbodiimide (DCC or DCCD), and catalysts, such as 1-Hydroxybenzotriazole (HOBt) and 4-Dimethylaminopyridine (DMAP) to furnish tryptamide. Alternatively, tryptamide is also achieved by reacting tryptamines with diacid chlorides. The resulting tryptamide is then extracted and purified from the reaction mixture. In a second step, the purified tryptamide compounds are refluxed with Phosphoryl chloride ($POCl_3$, aka phosphorus oxychloride) to yield a harmaline dimer compound, which is then extracted and purified from the reaction mixture. These two independent synthesis pathways in the traditional method consume time and money as the method requires purification of both the intermediate and final products.

In view of the foregoing, there is accordingly a need in the art for new synthesis methods for β-carboline adducts and harmaline dimer compounds that are time-efficient and cost-effective.

SUMMARY OF THE INVENTION

The present disclosure is concerned with novel β-carboline adducts and β-carboline dimer compounds comprising two β-carboline moieties and novel methods of synthesizing the same. As used herein, the terms "β-carboline moiety" and "β-carboline moieties" refers to a moiety (or moieties) having β-carboline as a basic chemical structure, namely the characteristic three-ringed structure containing a pyridine ring that is fused to an indole skeleton:

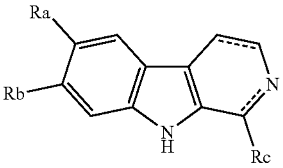

Where Ra, Rb, and Rc indicate various possible substitutions in the tricyclic moiety and the dashed line ---- indicates an optional position of a saturated or unsaturated bond in the pyridine ring. It is further contemplated that the nitrogen in the pyrrole ring of the indole can be substituted. Different levels of saturation are possible in the third ring which is indicated here in the structural formula by showing the optional double bonds in dashed lines. Further, the location of the double bonds may differ from the position indicated, i.e., it may rotate around any of the rings depending upon the substituents selected at the various carbon positions in the rings.

In one or more embodiments, the method of synthesizing a dimer or adduct compound comprises reacting an indole derivative having primary amine functionality with a diacid chloride or mono acid chloride in a suitable solvent system (with neutralizing base) and refluxing with a condensation reagent to yield a dimer or adduct product. In one or more embodiments, the reaction furnishes harmaline dimers or adducts. These harmaline compounds can be subsequently converted into harmine and tetrahydroharmine compounds using reducing or oxidizing agents. Thus, the methods of the invention can be used to synthesize a variety of tricyclic β-carboline adducts and dimers as described in more detail below.

In one or more embodiments, the first step of the mechanism involves reaction between tryptamine and diacid chloride to furnish tryptamide dimers. 2 equivalent of tryptamine reacts with 1 equivalent of diacid chloride and furnishes 1 equivalent of tryptamide dimer and 2 equivalents of HCl. Next, there is a reaction between phosphoryl chloride and tryptamide dimer intermediate to furnish harmaline dimer (Bischler-Napieralski reaction).

In one or more embodiments, the first step of the mechanism involves reaction between tryptamine and acid chloride to furnish tryptamide. 1 equivalent of tryptamine reacts with 1 equivalent of acid chloride and furnishes 1 equivalent of tryptamide and 1 equivalent of HCl. Next, there is a reaction between phosphoryl chloride and tryptamide intermediate to furnish harmaline adduct (Bischler-Napieralski reaction).

DETAILED DESCRIPTION

I. Adduct Compounds

Figure 1A:
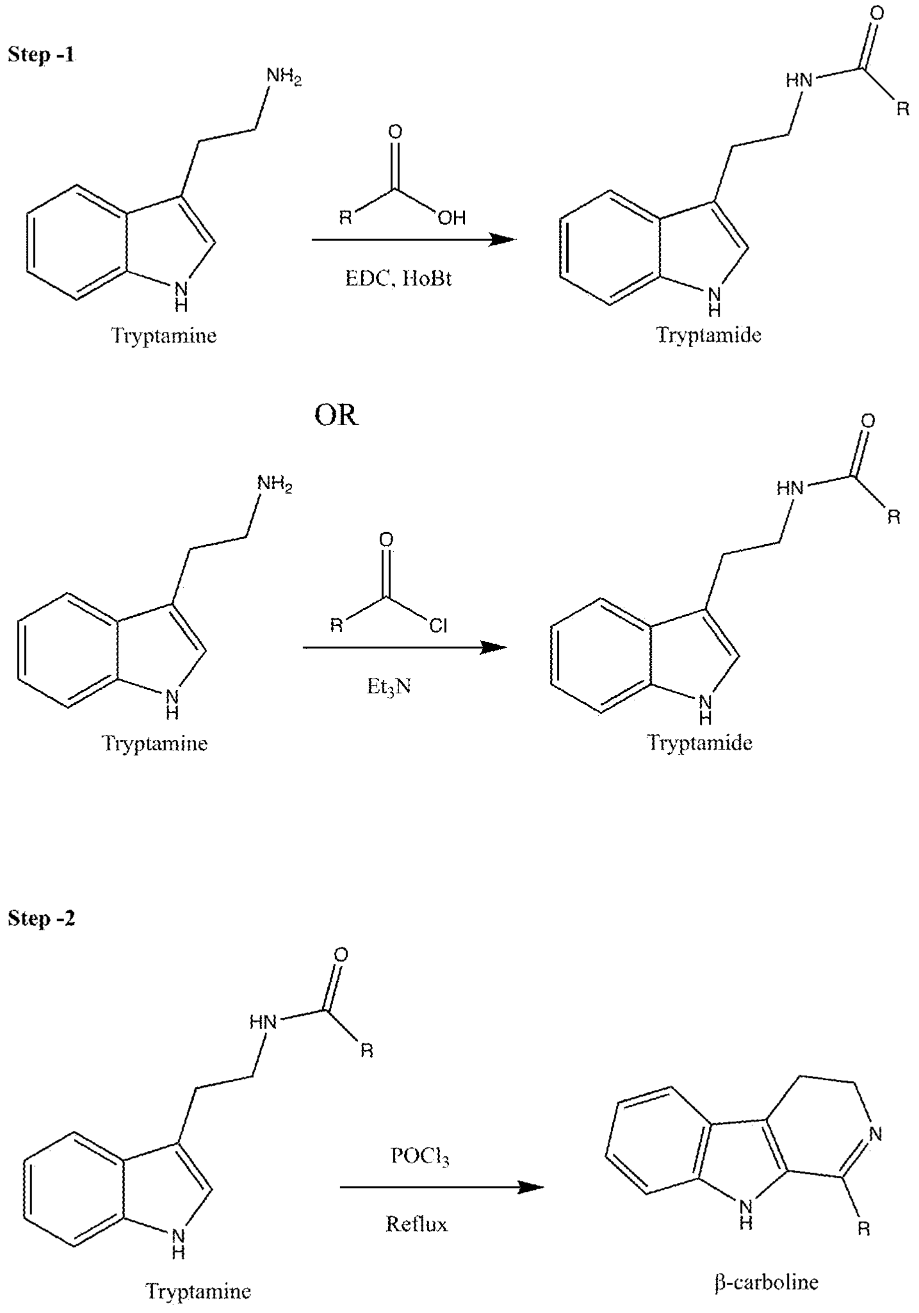
FIG. 1A (prior art)
FIG. 1A shows a traditional method used to synthesize a β-carboline.
Figure 1B:
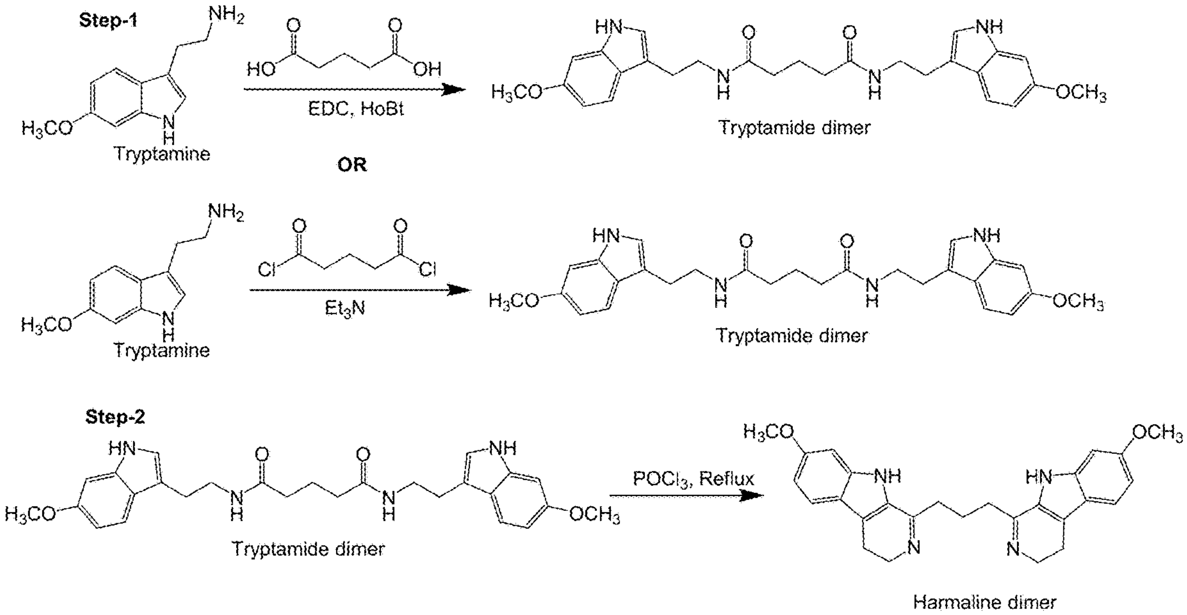
FIG. 1B (prior art)
FIG. 1B shows a traditional synthesis method for synthesizing a harmaline dimer molecule.

In one or more embodiments, the novel adduct compounds comprise β-carboline moieties with hydrocarbon chain connecting with a wide range of chemical moieties depending on the selected acid chloride. Although any desired β-carboline moieties are suitable, the preferred β-carboline moieties include harmine, harmaline, and tetrahydro harmine moieties, forming the following a) harmine, b) harmaline, or c) tetrahydroharmine compounds:

a)

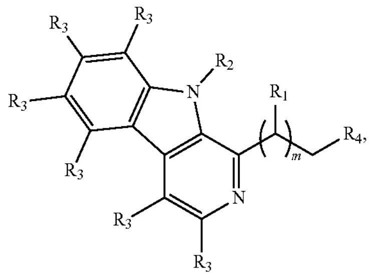

b)

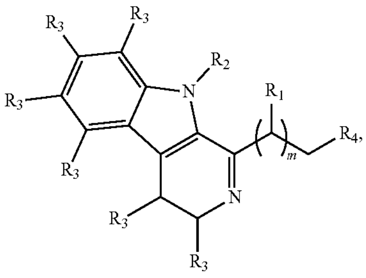

or c)

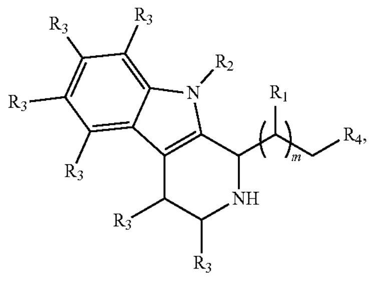

where m is 0-20, and preferably at least 1, and each $R_1$, $R_2$, $R_3$ and $R_4$ is independently selected from the group of possible options in the table below.

TABLE

| Adduct Substituents | |
|---|---|
| Group | Possible substitutions |
| $R_1$ | H, halogens, Sulfur, Thiols, alkyls(C1-C15), hydroxy, H-donor groups (carboxylic acids, amine and amides), H-bond acceptor (Ethers, Esters, Aldehydes, ketones), Aromatic ring with size from 4-10 carbons, Heterocyclic ring with size 4-10 atoms, Aromatic or heterocycle rings with substitutions like halogens, alkyls(C1-C15), hydroxy, H-donor groups and H-bond acceptor, Fused heterocyclic rings (Thioridazine, purines, coumarins, Indoles, Indazole). |
| $R_2$ | H, halogens (charged and neutral), Sulfur, Thiols, alkyls(C1-C15), hydroxy, H H-donor groups (e.g., carboxylic acids, amines, and amides), H-bond acceptor groups (e.g., ethers, esters, aldehydes, or ketones), C4-C10 Aromatic ring with ring size from 4-10 carbons, Heterocyclic ring with ring size 4-10 atoms, substituted aromatic or heterocycle rings (e.g., with halogens, alkyls (C1-C15), hydroxy, H-donor groups, or H-bond acceptor), Fused heterocyclic rings (Thioridazine, purines, coumarins, Indoles, Indazole), salts of HCl or TFA or $CH_3I$, metals like Cu, Pd, Bi, Fe, Zn. |
| $R_3$ | Hydrogen, Oxygen, halogens, Sulfur, sulfonyl chloride, Sulphonic acid, thiols, alkyls (C1-C15), hydroxy, H-donor groups (carboxylic acids, amine and amides), H-bond acceptor (Ethers, Esters, Aldehydes, ketones), Nitro groups, hydroxy, Alkoxy (C1-C15), H-donor groups (e.g., carboxylic acids, amines, and amides), H-bond acceptor groups (e.g., ethers, esters, aldehydes, or ketones), Aromatic, Antiaromatic, or non-aromatic compounds up to 10 atoms, for example, Furan, imidazole, Benzene, Pyridine, Indole, Indazole, Cyclooctatetraene, [10]annulene, Pentalene, Indene, Naphthalene, Heptalene, Biphenylene, as-indacene, acenaphthylene, : fluorene, phenalene, Anthracene, Pyrene, Fluoranthene, Imidazopyridines, Pyrazopyridines, Oxazolopyridines, Isooxazolopyridines, Cyclopropane, cyclopentane, methyl, ethyl, propyl, isopropyl, pentadiene, hexane, or hexene, any of which may or may not be substituted such as with halogens, alkyls(C1-C15), hydroxy, H-donor groups (e.g., carboxylic acids, amines, and amides), H-bond acceptor groups (e.g., ethers, esters, aldehydes, or ketones). Fused polycyclic and heterocyclic rings, such as thioridazine, purines, coumarins, indoles, or indazole, with substitutions at one or more carbons of the rings. |
| $R_4$ | halogens (charged and neutral), Thiols, hydroxy, alkyls(C1-C15), H-donor groups (e.g., carboxylic acids, amines, and amides), H-bond acceptor groups (e.g., ethers, esters, aldehydes, or ketones), Oxygen (e.g., with double bond), Nitrogen (e.g., with double bond or triple bond), thiazol-2-amine, morpholine, pyrimidine-2,4(1H,3H)-dione, pyrimidine-2,4(1H,3H)-dione, 1-tosyl-1H-pyrrole, 1-chloro-3-(methylsulfonyl)benzene, 4-(thiazol-2-yl)morpholine, pyrimidine-2,4-diamine, Aromatic ring with ring size from 4-10 carbons, Heterocyclic ring with ring size 4-10 atoms, Saturated and unsaturated cyclic hydrocarbon with ring size from 3-10 (e.g., cyclo propane, azetidine, azetidine, cyclo butane), Fused heterocyclic rings (e.g., thioridazine, purines, coumarins, indoles, indazole), Saturated and unsaturated cyclic hydrocarbon with ring size from 3-10, any of which may or may not be substituted such as with halogens, alkyls(C1-C15), hydroxy, H-donor groups (e.g., carboxylic acids, amines, and amides), H-bond acceptor groups (e.g., ethers, esters, aldehydes, or ketones). |

These tricyclic β-carboline adduct compounds can be synthesized using the general process of reacting 1 equivalent tryptamine with 1 equivalent acid chloride in acetonitrile as the solvent system to furnish 1 equivalent of tryptamide intermediate (and 1 equivalent of HCl). The amide intermediate compound reacts with a condensation reagent (such as $P_2O_5$, $POCl_3$ or $ZnCl_2$) via an initial dehydration step of the amide, followed by a cyclization to ultimately close the chain and form the pyridine ring in the indole intermediate moiety in the adduct. In general, the reaction can be carried out over a time period ranging from 15 minutes to 48 hours, and reaction temperatures can range from −5° C. to 105° C.

In more detail, a tryptamine is reacted with an acid chloride in acetonitrile. Any indole derivative with primary amine functionality may be used, provided the amine has at least two carbons between the cyclic structure and the amine for subsequent cyclization. Tryptamine or derivatives thereof may be used in the above-described method, and it is preferred that the amine is compatible with the acid chloride used. In one or more embodiments, the amine may be, but is not limited to, aromatic or heterocyclic ethyl amines (e.g., substituted or unsubstituted tryptamines, e.g., methoxy-tryptamines, ethoxy-tryptamines, as well as 2-pyrrolyl ethylamine, and 2-phenylethylamine).

In particular, the starting indole derivative with primary amine functionality is mixed with acetonitrile in a reaction vessel, for example, 6-methoxy tryptamine is added to a flask equipped with a condenser, preferably in a glove bag under nitrogen. Acetonitrile is a unique solvent for this reaction because it is a solvent in which the reagents are soluble, but which the intermediate and final reaction products are not, thus facilitating formation of the reaction product precipitates as the reaction progresses. Pure, non-diluted acetonitrile is used in the reaction. Preferably, the weight ratio of tryptamine to acetonitrile is from about 1:1 to about 1:1000. An organic base (e.g., pyridine, triethylamine, or even NaOH) as a neutralization agent is added to the flask in a weight ratio of from about from about 1:1 to about 1:10. This is used to neutralize the HCl byproduct in the reaction. Once the initial reagents are mixed in the solvent system, the acid chloride is added to the solution to initiate the reaction. The acid chloride will be reacted with the starting indole derivative in a weight ratio of from about 3:1 to about 1:1 indole amine:acid chloride. The above reagents can be added or mixed in any order in the solvent system, so long as the acid chloride is added last.

Figure 2A:
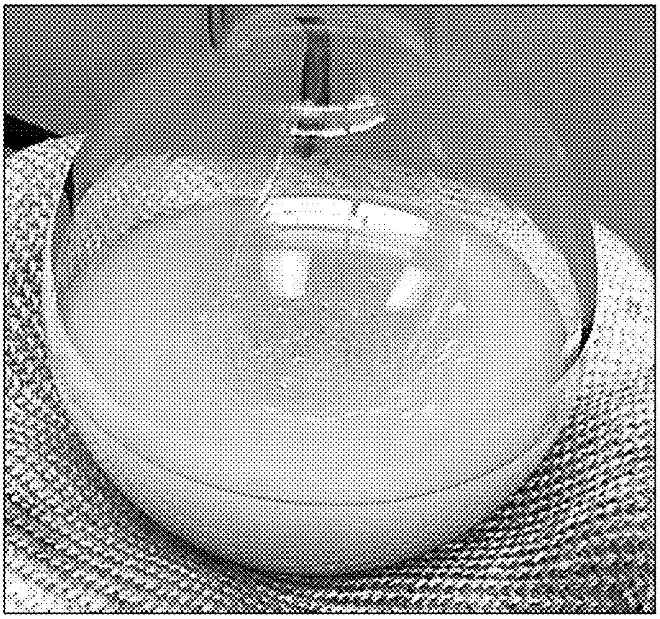
FIG. 2A shows a photograph of the flask containing the cloudy reaction solution that indicates formation of intermediate adduct or dimer.
Figure 2B:
FIG. 2B shows a photograph of the cloudy solution from FIG. 2A in the same flask which immediately turns a transparent reddish color instantly upon adding the condensation reagent (in this case $POCl_3$).
Figure 2C:
FIG. 2C shows a photograph of the progressing reaction in which the transparent reddish solution from FIG. 2B slowly turns cloudy in the same flask.
Figure 2D:
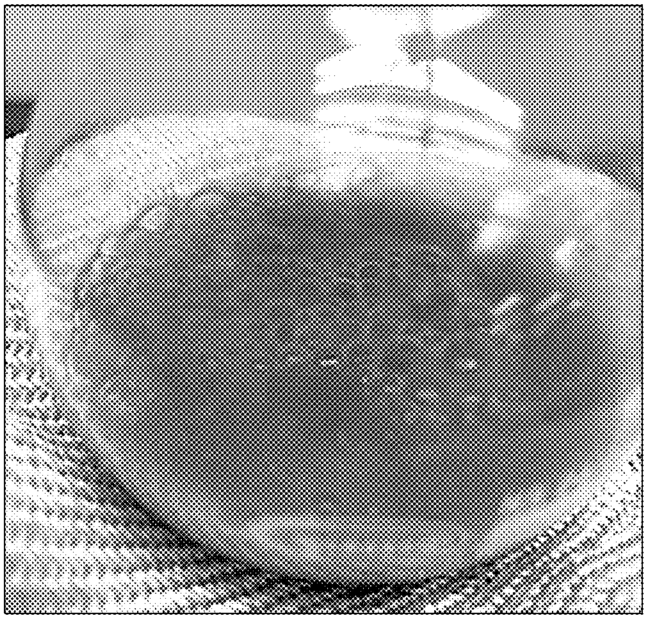
FIG. 2D shows a photograph of the progressing reaction in the same flask in which the reaction solution slowly turns into a cloudy yellow colored solution indicating the formation of desired adduct or dimer reaction product which is not soluble in the solvent system and thus precipitates out of the solution as the reaction products are formed.

The resultant solution is heated to reflux at atmospheric (normal) pressure and a temperature about −5° C. to about 105° C., preferably about 10° C. to about 100° C., more preferably about 25° C. to about 95° C. for about 15 min to about 12 hours, preferably from about 15 minutes to about 3 hours, or until precipitation is observed in the solution. One of ordinary skill in the art would understand that, during this period, the reflux temperature and reflux time may need to be adjusted according to the properties of the indole amine and acid chloride selected. The reaction progresses and the intermediate products are formed as indicated by the solution turning from an initially transparent yellow color into a cloudy solution and, in some cases, a pale yellow color, as shown in FIG. 2A. After this period, the condensation agent is slowly added to the flask (while continuing heating), in a weight ratio of condensation agent to amine of about 1:2 to about 1:50. Then, reflux is continued for about 60 minutes to about 12, preferably from about 60 minutes to about 3 hours, or until precipitation is observed (up to 24 hours). Upon addition of the condensation reagent, the cloudy reaction solution containing the intermediate products initially (and immediately) turns into a reddish transparent solution, as shown in FIG. 2B. As the reaction progresses, solids start precipitating out of the solution and the solution and the transparent solution slowly turns into a cloudy yellowish solution, as shown in FIG. 2C and then FIG. 2D. Once the reaction is complete, the resulting solution is cooled to room temperature. Typically, the reaction completion is visible by precipitation of the reaction product out of the solution. Further cooling may be achieved by keeping the flask in an ice bath, preferably for 30 minutes. The resulting adduct compound is collected using vacuum filtration and washed with a cold solvent, preferably ethanol. If impurities are detected, column purification and recrystallization may be used to remove salts formed during the reaction. The reaction advantageously does not require or involve the addition of any water, and preferably is a "dry" as possible, and excludes water or any aqueous solvents from the reaction solution. Further, the reaction does not involve any isolation, filtering, or purification of any intermediate reaction products. The only filtering or purification occurs at the end of the reaction on the final reaction product. Further, the reaction achieves near 100% conversion of the initial starting reactants into the final reaction product, resulting in much higher yields as compared to previous synthesis schemes. Thus, there is less than 5 wt %, preferably less than 1 wt % of any of the initial reactants in the reaction solution at the end of the reaction, preferably less than 0.5 wt %, more preferably about 0.1 wt %. Preferably, the reaction has a final reaction product yield of 60% or greater, as compared to total amount of starting reactants (taken as 100%), preferably 75% or greater, even more preferably 80% or greater, even more preferably 85% or greater, even more preferably 95% or greater, and even more preferably 99% or greater This is much higher than traditional two-step synthesis methods where yields of the final reaction product are less than 60% (i.e., at least 40% or more of the starting reactants are lost).

Suitable acid chloride for adduct synthesis include any acid chloride comprising an alkyl chain of 2 or more carbons. Non-limiting examples include acetyl chloride ($C_2H_3ClO$) propionyl chloride ($C_3H_5ClO$), 3-Chloropropionyl chloride ($C_3H_4ClO$), butyryl chloride ($C_4H_7ClO$), Valeroyl chloride ($C_5H_9ClO$), Isovaleryl chloride ($C_5H_9ClO$), 2-Methylbutyryl chloride ($C_5H_9ClO$), hexanoyl chloride ($C_6H_{11}ClO$), heptanoyl chloride ($C_7H_{13}ClO$), Octonoyl chloride ($C_8H_{15}ClO$), nonanoyl chloride ($C_9H_{17}ClO$), decanoyl chloride ($C_{10}H_{19}ClO$), undecanoyl chloride ($C_{11}H_{21}ClO$), Lauroyl chloride ($C_{12}H_{23}ClO$), tridecanoyl chloride ($C_{13}H_{25}ClO$), tetradecanoyl chloride ($C_{14}H_{27}ClO$), pentadecanoyl chloride ($C_{15}H_{29}ClO$), palmitoyl chloride ($C_{16}H_{31}ClO$), heptadecanoyl chloride ($C_{17}H_{33}ClO$), stearoyl chloride ($C_{18}H_{35}ClO$), nonadecanoyl chloride ($C_{19}H_{37}ClO$), icosanoyl chloride ($C_{20}H_{39}ClO$), and Thiophene-2-acetyl Chloride ($C_6H_5ClOS$). For acid chloride not commercially-available to purchase, they can be synthesized using respective carboxylic acids to react with thionyl chloride to furnish acid chlorides. Exemplary acid chlorides and the corresponding adducts furnished when reacted with the tryptamine are shown in the table below.

TABLE

| Acid Chlorides | | |
|---|---|---|
| Acid Chloride | Acid Chloride Structure | Adduct Structure |
| 6-hydroxyhexanoyl chloride | 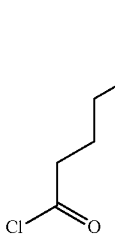 | 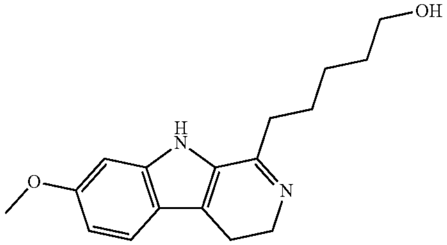 Chemical Formula: $C_{17}H_{22}N_2O_2$ Molecular Weight: 286.38 |

TABLE-continued

| Acid Chlorides | | |
|---|---|---|
| Acid Chloride | Acid Chloride Structure | Adduct Structure |
| 2-(1H-1,2,4-triazol-1-yl)acetyl chloride | 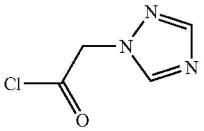 | 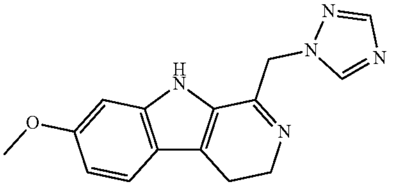 Chemical Formula: $C_{15}H_{15}N_5O$ Molecular Weight: 281.32 |
| 2-(piperidin-1-yl)acetyl chloride | 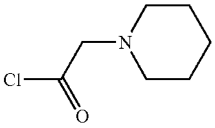 | 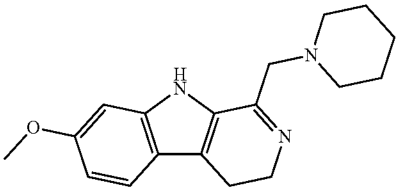 Chemical Formula: $C_{18}H_{23}N_3O$ Molecular Weight: 297.40 |
| 4-aminobutanoyl chloride | 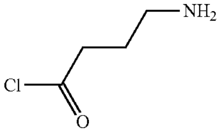 | 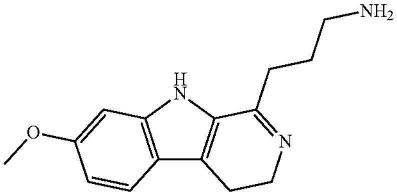 Chemical Formula: $C_{15}H_{19}N_3O$ Molecular Weight: 257.34 |
| methyl 5-chloro-5-oxopentanoate | 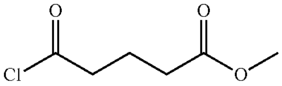 | 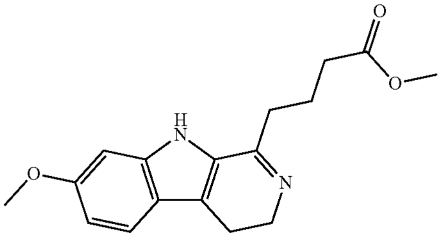 Chemical Formula: $C_{17}H_{20}N_2O_3$ Molecular Weight: 300.36 |
| 5-chloro-5-oxopentanoic acid | 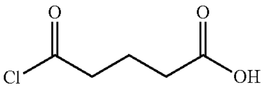 | 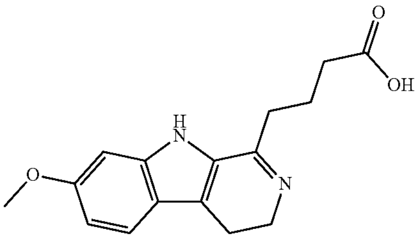 Chemical Formula: $C_{16}H_{18}N_2O_3$ Molecular Weight: 286.33 |

TABLE-continued

| Acid Chlorides | | |
|---|---|---|
| Acid Chloride | Acid Chloride Structure | Adduct Structure |
| 4-mercaptobutanoyl chloride | 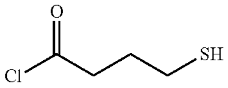 | 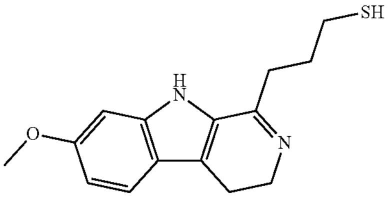 Chemical Formula: $C_{15}H_{18}N_2OS$ Molecular Weight: 274.38 |
| 3-cyclobutylpropanoyl chloride | 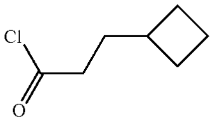 | 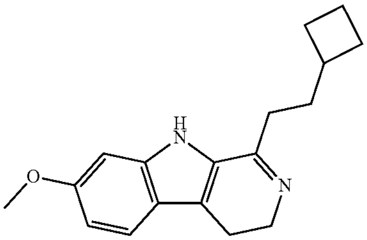 Chemical Formula: $C_{18}H_{22}N_2O$ Molecular Weight: 282.17 |
| 2-(thiophen-2-yl)acetyl chloride | 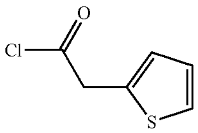 | 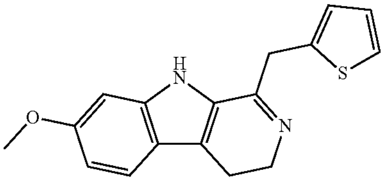 Chemical Formula: $C_{17}H_{16}N_2OS$ Molecular Weight: 296.10 |
| 2-cyclobutylacetyl chloride | 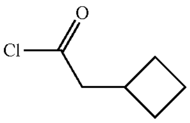 | 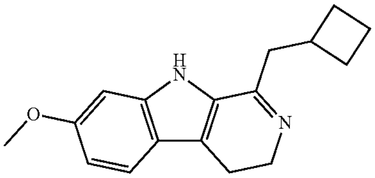 Chemical Formula: $C_{17}H_{20}N_2O$ Molecular Weight: 268.16 |
| 3-cyclopropylpropanoyl chloride | 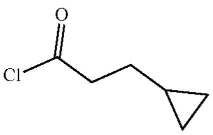 | 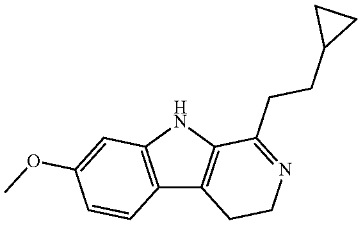 Chemical Formula: $C_{17}H_{20}N_2O$ Molecular Weight: 268.16 |

TABLE-continued

| Acid Chlorides | | |
|---|---|---|
| Acid Chloride | Acid Chloride Structure | Adduct Structure |
| 3-cyclopentylpropanoyl chloride | 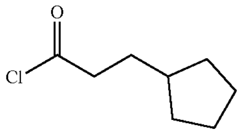 | 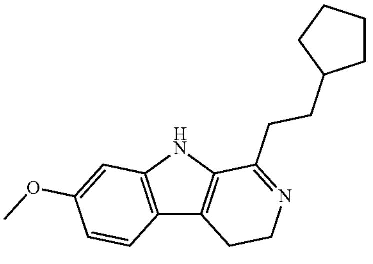<br>Chemical Formula: $C_{19}H_{24}N_2O$<br>Molecular Weight: 296.19 |

2. Dimer Compounds

In one or more embodiments, the novel dimer compounds comprise two β-carboline moieties linked via a "tether," which, as used herein, refers to the hydrocarbon chain connecting the two moieties. Typically, the carbon chain is bonded to the respective methyl substituents of the β-carboline moieties, which then become part of the tether. Although any desired β-carboline moieties are suitable, the preferred β-carboline moieties include harmine, harmaline, and tetrahydro harmine moieties, forming the following a) harmine, b) harmaline, or c) tetrahydro harmine dimers:

a)

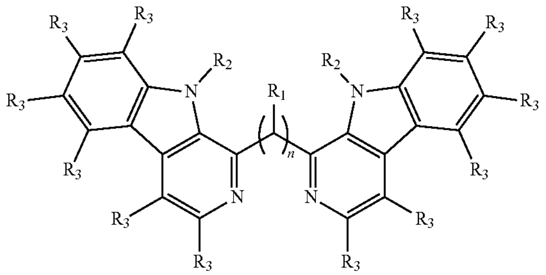

-continued b)

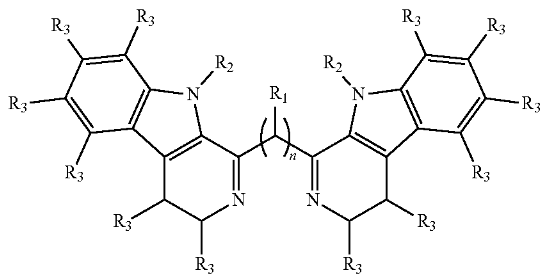

c)

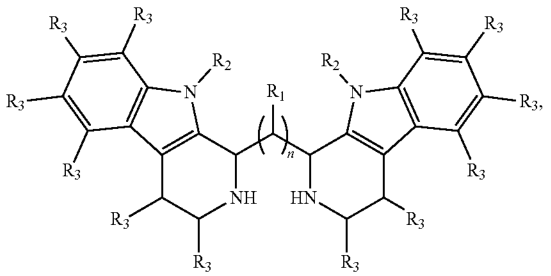

where n is 3-22, preferably n is at least 3; and each $R_1$, $R_2$, and $R_3$ is independently selected from the group of possible options in the table below.

TABLE

| Dimer Substituents | |
|---|---|
| Group | Possible substitutions |
| $R_1$ | H, halogens, Sulfur, Thiols, alkyls(C1-C15), hydroxy, H-donor groups (carboxylic acids, amine and amides), H-bond acceptor (Ethers, Esters, Aldehydes, ketones), Aromatic ring with size from 4-10 carbons, Heterocyclic ring with size 4-10 atoms, Aromatic or heterocycle rings with substitutions like halogens, alkyls(C1-C15), hydroxy, H-donor groups and H-bond acceptor, Fused heterocyclic rings (Thioridazine, purines, coumarins, Indoles, Indazole). |
| $R_2$ | H, halogens (charged and neutral), Sulfur, Thiols, alkyls(C1-C15), hydroxy, H-donor groups (carboxylic acids, amine and amides), H-bond acceptor (Ethers, Esters, Aldehydes, ketones), Aromatic ring with size from 4-10 carbons, Heterocyclic ring with size 4-10 atoms, Aromatic or heterocycle rings with substitutions like halogens, alkyls(C1-C15), hydroxy, H-donor groups and H-bond acceptor, Fused heterocyclic rings (Thioridazine, purines, coumarins, Indoles, Indazole), salts of HCl or TFA or $CH_3I$, metals like Cu, Pd, Bi, Fe, Zn. |

TABLE-continued

| Dimer Substituents | |
|---|---|
| Group | Possible substitutions |
| $R_3$ | H, halogens, Sulfur, Thiols, Oxygen, alkyls(C1-C15), hydroxy, H-donor groups (carboxylic acids, amine and amides), H-bond acceptor (Ethers, Esters, Aldehydes, ketones), Aromatic ring with size from 4-10 carbons, Heterocyclic ring with size 4-10 atoms, Aromatic or heterocycle rings with substitutions like halogens, alkyls(C1-C15), hydroxy, H-donor groups and H-bond acceptor. Fused heterocyclic rings, such as Thioridazine, purines, coumarins, Indoles, Indazole. |

In the structures, any carbon in the chain or tether connecting the tricyclic moieties can be substituted or unsubstituted.

Advantageously, in the novel dimer compounds the tether has a length of n is at least 3, wherein the substituent $R_1$ may be positioned at any carbon position (or multiple carbon positions) along the tether. Further, the tether may include one or more substitutions ($R_1$) along the tether (again at any carbon position), and each substituent $R_1$ may be independently selected from the options above. In addition, the structures having this tether length notably all differ from the tricyclic β-carboline dimer compounds disclosed in U.S. Patent Publication No. 2022/0033417. Particularly, these tricyclic β-carboline dimer compounds previously disclosed do not bear aromatic rings (e.g., benzene, imidazole, pyridine, purine, coumarin, indole, etc.) or non-aromatic heterocyclic rings at any carbon position along the tether.

In embodiments where the novel dimer compound comprises two harmaline moieties (e.g., a harmaline dimer), the novel dimer compound may be selected from the group of one or more of the following compounds:

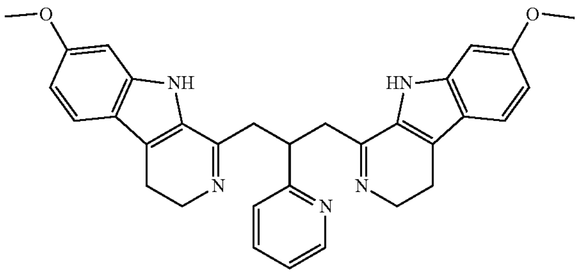

GK517.2
Chemical Formula: $C_{32}H_{31}N_5O_2$
Molecular Weight: 517.63

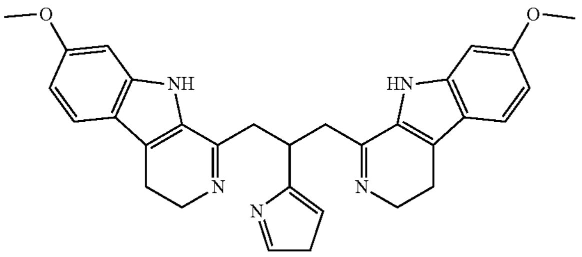

GK505.2Py
Chemical Formula: $C_{31}H_{31}N_5O_2$
Molecular Weight: 505.62

-continued

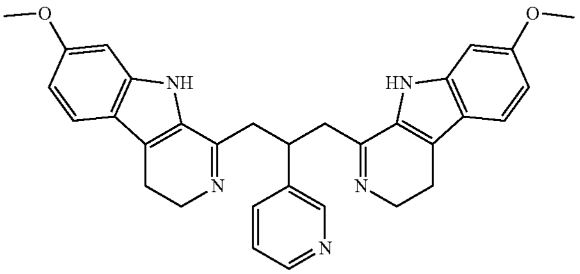

GK517.3
Chemical Formula: $C_{32}H_{31}N_5O_2$
Exact Mass: 517.25

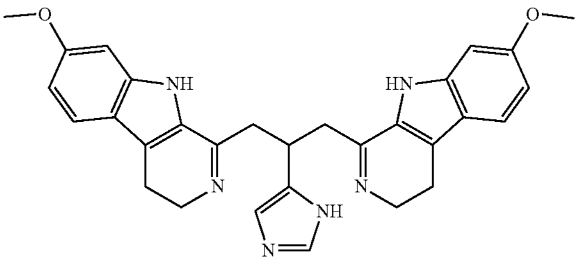

GK506.2Im
Chemical Formula: $C_{30}H_{30}N_6O_2$
Exact Mass: 506.24

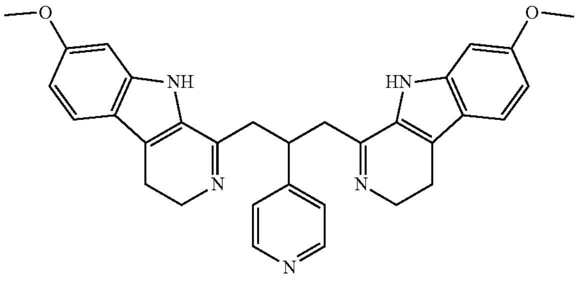

GK517.4
Chemical Formula: $C_{32}H_{31}N_5O_2$
Molecular Weight: 517.63

-continued

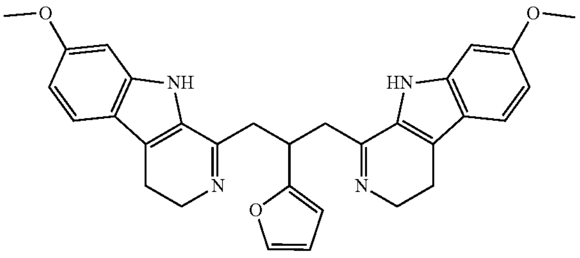

GK506.2Fn
Chemical Formula: $C_{31}H_{30}N_4O_3$
Exact Mass: 506.23

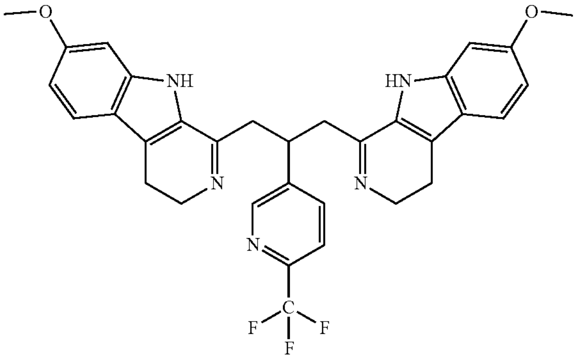

GK585
Chemical Formula: $C_{33}H_{30}F_3N_5O_2$
Molecular Weight: 585.63

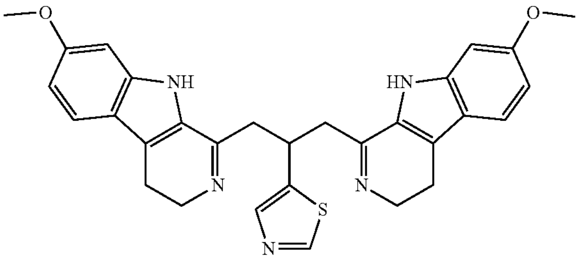

GK524
Chemical Formula: $C_{30}H_{29}N_5O_2S$
Molecular Weight: 523.65

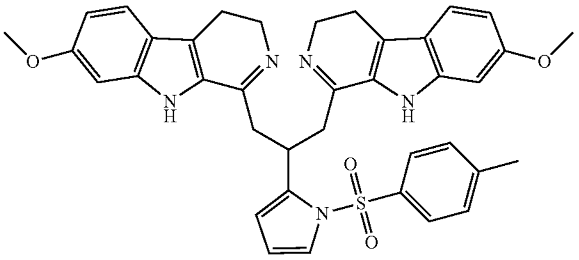

GK659
Chemical Formula: $C_{38}H_{37}N_5O_4S$
Molecular Weight: 659.80

-continued

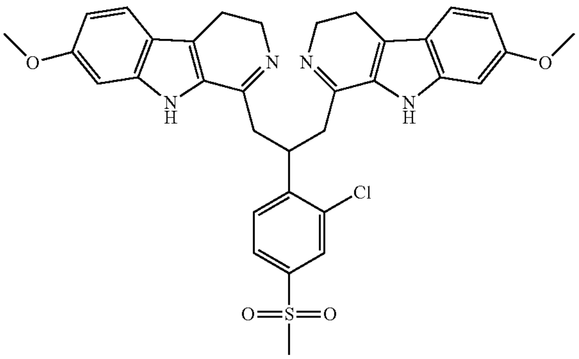

GK629
Chemical Formula: $C_{34}H_{33}ClN_4O_4S$
Molecular Weight: 629.17

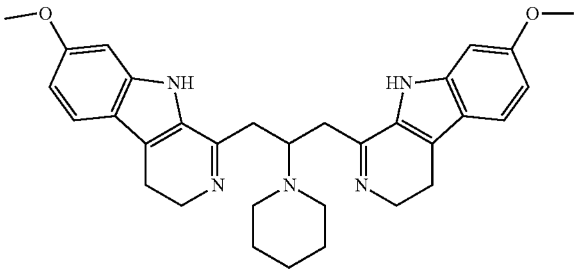

GK523
Chemical Formula: $C_{32}H_{37}N_5O_2$
Molecular Weight: 523.68

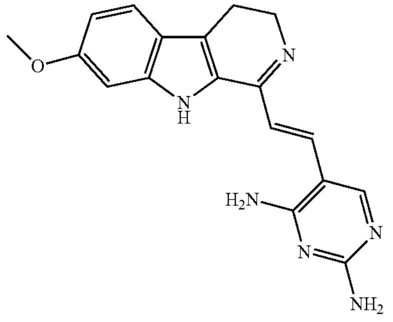

GK334
Chemical Formula: $C_{18}H_{18}N_6O$
Molecular Weight: 334.38

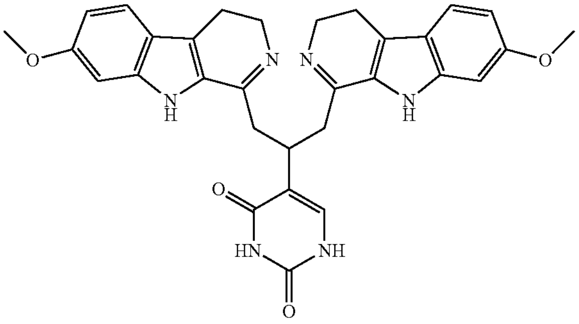

GK550
Chemical Formula: $C_{31}H_{30}N_6O_4$
Molecular Weight: 550.62

-continued

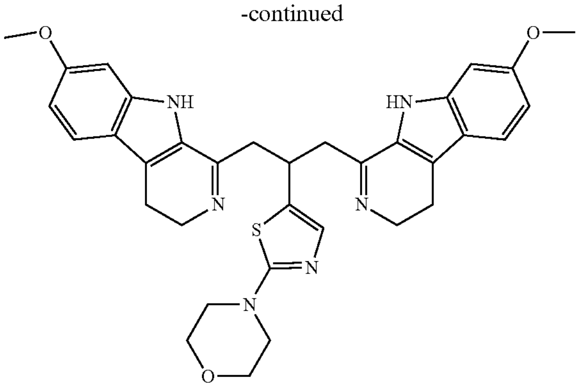

GK608
Chemical Formula: $C_{34}H_{36}N_6O_3S$
Molecular Weight: 608.76

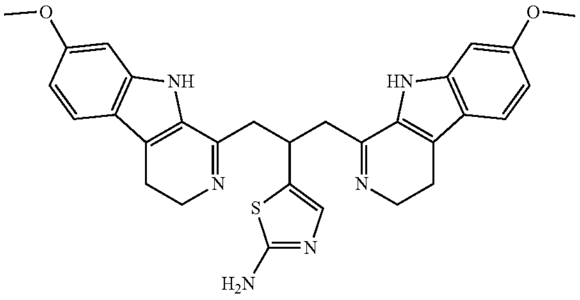

GK538
Chemical Formula: $C_{30}H_{30}N_6O_2S$
Molecular Weight: 538.67

To synthesize the above-described dimer compounds, a tryptamine is reacted with a diacid chloride in acetonitrile to create an amide dimer intermediate compound which reacts with a condensation reagent (such as $P_2O_5$, $POCl_3$ or $ZnCl_2$) via an initial dehydration step of the amide, followed by a cyclization to ultimately close the chain and form the pyridine ring on each indole intermediate moiety in the dimer. In particular, the starting indole derivative with primary amine functionality is mixed with acetonitrile as the solvent system in a reaction vessel, for example, 6-methoxy tryptamine is added to a flask equipped with a condenser, preferably in a glove bag under nitrogen, and acetonitrile is then added to the flask. Acetonitrile is an ideal solvent in which the reagents are soluble, but which the reaction product is not, thus facilitating formation of the reaction product precipitates as the reaction progresses. Pure, non-diluted acetonitrile is used in the reaction. Preferably, the weight ratio of Tryptamine to solvent is from about 1:1 to about 1:1000. An organic base (e.g., pyridine, triethylamine, or even NaOH) as a neutralization agent is added to the flask in a weight ratio of from about from about 1:1 to about 1:10. This is used to neutralize HCl, which is a byproduct in the reaction. Once the initial reagents are mixed in the solvent system, the diacid chloride is added to the solution to initiate the reaction. The diacid chloride will be selected depending on the desired tether length for the dimer. The diacid chloride will be reacted with the starting indole derivative in a weight ratio of from about 3:1 to about 1:1 indole amine:diacid chloride. The above reagents can be added or mixed in any order in the solvent system, so long as the diacid chloride is added last. In general, the reaction can be carried out over a time period ranging from 15 minutes to 48 hours, and reaction temperatures can range from −5° C. to 105° C.

The resultant solution is heated to reflux at atmospheric (normal) pressure and a temperature about −5° C. to about 105° C., preferably about 10° C. to about 100° C., more preferably about 25° C. to about 95° C. for about 15 min to about 12 hours, preferably from about 15 minutes to about 3 hours, or until precipitation is observed in the solution. One of ordinary skill in the art would understand that, during this period, the reflux temperature and reflux time may need to be adjusted according to the properties of the indole amine and diacid chloride selected. The reaction progresses and the intermediate products are formed as indicated by the solution turning from an initially transparent or clear yellow color into a cloudy solution and, in some cases, a pale yellow color, as shown in FIG. 2A. After this period, the condensation agent is slowly added to the flask, in a weight ratio of condensation agent to amine of about 1:2 to about 1:50. Then, reflux is continued for about 60 minutes to about 12, preferably from about 60 minutes to about 3 hours, or until precipitation is observed (up to 24 hours). Upon addition of the condensation reagent, the cloudy reaction solution containing the intermediate products initially (and immediately) turns into a reddish transparent or clear solution, as shown in FIG. 2B. As the reaction progresses, solids start precipitating out of the solution and the solution and the transparent solution slowly turns into a cloudy yellowish solution, as shown in FIG. 2C and finally FIG. 2D. Once the reaction is complete, the resulting solution is cooled to room temperature. Typically, the reaction completion is visible by precipitation of the reaction product out of the solution. Further cooling may be achieved by keeping the flask in an ice bath, preferably for 30 minutes. The resulting dimer compound is collected using vacuum filtration and washed with a cold solvent, preferably ethanol. If impurities are detected, column purification and recrystallization may be used to remove salts formed during the reaction. The reaction advantageously does not require or involve the addition of any water, and preferably is a "dry" as possible, and excludes water or any aqueous solvents from the reaction solution. Further, the reaction does not involve any isolation, filtering, or purification of any intermediate reaction products. The only filtering or purification occurs at the end of the reaction on the final reaction product. Further, the reaction achieves near 100% conversion of the initial starting reactants into the final reaction product, resulting in much higher yields as compared to previous synthesis schemes. Thus, there is less than 5 wt %, preferably less than 1 wt % of any of the initial reactants in the reaction solution at the end of the reaction, preferably less than 0.5 wt %, more preferably about 0.1 wt %. Preferably, the reaction has a final reaction product yield of 60% or greater, as compared to total amount of starting reactants (taken as 100%), preferably 75% or greater, even more preferably 80% or greater, even more preferably 85% or greater, even more preferably 95% or greater, and even more preferably 99% or greater This is much higher than traditional two-step synthesis methods where yields of the final reaction product are less than 60% (i.e., at least 40% or more of the starting reactants are lost).

Any indole derivative with primary amine functionality may be used, provided the amine has at least two carbons between the cyclic structure and the amine for subsequent cyclization. Tryptamine or derivatives thereof may be used in the above-described method, and it is preferred that the amine is suitable with the diacid chloride used. In one or more embodiments, the amine may be, but is not limited to, aromatic or heterocyclic ethyl amines (e.g., substituted or unsubstituted tryptamines, e.g., methoxy-tryptamines, ethoxy-tryptamines, as well as 2-pyrrolyl ethylamine, and 2-phenylethylamine).

Suitable diacid chlorides include any diacid chloride comprising four or more carbons. Non-limiting examples include succinyl chloride ($C_4H_4Cl_2O_2$), glutaryl chloride ($C_5H_6Cl_2O_2$), adipoyl dichloride ($C_6H_8Cl_2O_2$), heptanedioyl dichloride ($C_7H_{10}Cl_2O_2$), Octanedioyl dichloride ($C_8H_{12}Cl_2O_2$) nonanedioyl dichloride ($C_9H_{14}Cl_2O_2$), decanedioyl dichloride ($C_{10}H_{16}Cl_2O_2$), undecanedioyl dichloride ($C_{11}H_{18}Cl_2O_2$), dodecanedioyl dichloride ($C_{12}H_{20}Cl_2O_2$), tridecanedioyl dichloride ($C_{13}H_{22}Cl_2O_2$), tetradecanedioyl dichloride ($C_{14}H_{24}Cl_2O_2$), pentadecanedioyl dichloride ($C_{15}H_{26}Cl_2O_2$), hexadecanedioyl dichloride ($C_{16}H_{28}Cl_2O_2$), docosanedioic acid dichloride ($C_{22}H_{40}Cl_2O_2$)). Preferably, a diacid chloride comprising five or more carbons (e.g., glutaryl chloride) is used. In embodiments where the diacid chloride comprises five or more carbons, the diacid chloride may have one or more substituents (such as the $R_1$ substituents described above) at any one of its $CH_2$ carbons.

In embodiments where the novel dimer compound synthesized is a harmaline dimer, the harmaline dimer may be converted into a harmine dimer or tetrahydro harmine dimer using diacid-catalyzed syntheses of harmaline to harmine in the presence of 2,3-dichloro-5,6-dicyano-1,4-benzoquinone (DDQ) as described in U.S. Pat. No. 11,578,070, filed Sep. 1, 2020, incorporated by reference herein.

Figure 3:
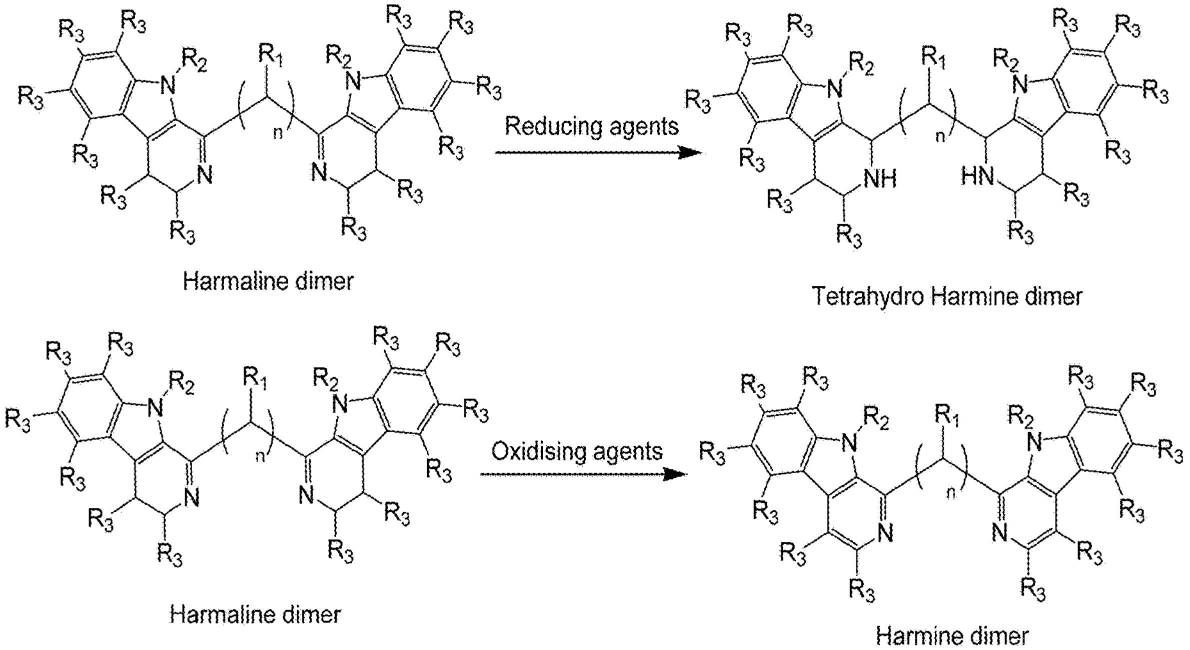
FIG. 3 shows synthesis of Tetrahydro Harmine dimer (Top), Harmine dimers (Bottom) from Harmaline dimers with tether length n=3-22.

In one or more embodiments, a harmine dimer or tetrahydro harmine dimer can be furnished by treating the harmaline dimer with an oxidizing agent(s) or reducing agent(s), as shown in FIG. 3.

The present disclosure also contemplates variations on the foregoing adduct or dimer structures, including isomers, tautomers, enantiomers, esters, derivatives, metal complexes, prodrugs, solvates, metabolites, and pharmaceutically acceptable salts thereof. "Isomers" refers to each of two or more compounds with the same formula but with at different arrangement of atoms, and includes structural isomers and stereoisomers (e.g., geometric isomers and enantiomers); "tautomers" refers to two or more isometric compounds that exist in equilibrium, such as keto-enol and imine and enamine tautomers; "derivatives" refers to compounds that can be imagined to arise or actually be synthesized from a defined parent compound by replacement of one atom with another atom or a group of atoms; "solvates" refers to interaction with a defined compound with a solvent to form a stabilized solute species; "metabolites" refers to a defined compound which has been metabolized in vivo by digestion or other bodily chemical processes; "prodrugs" refers to defined compound which has been generated by a metabolic process; and "pharmaceutically acceptable salts" with reference to the components means salts of the components which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts Properties, and Use, P. H. Stahl & C. G. Wermuth eds., ISBN 978-3-90639-058-1 (2008).

Compositions comprising (consisting essentially or even consisting of) above-described compounds are also contemplated. The compositions may include additional pharmaceutically-acceptable ingredients and/or vehicles as a base carrier composition in which the active ingredients are dispersed. As used herein, the term "pharmaceutically-acceptable" means not biologically or otherwise undesirable, in that it can be administered to a subject without excessive toxicity, irritation, or allergic response, and does not cause any undesirable biological effects or interact in a deleterious manner with any of the other components of the composition in which it is contained. The terms "vehicle" or "carrier," as used herein, mean one or more compatible base compositions with which the active ingredient (e.g., above-described compounds) is combined to facilitate the administration of ingredient, and which is suitable for administration to a patient. Such preparations may also routinely contain salts, buffering agents, preservatives, and optionally other therapeutic ingredients or adjuvants. The carrier would naturally be selected to minimize any degradation of the active ingredient and to minimize any adverse side effects in the subject, as would be well known to one of ordinary skill in the art. Pharmaceutically-acceptable ingredients include those acceptable for veterinary use as well as human pharmaceutical use. The term "adjuvant" is used herein to refer to substances that have immunopotentiating effects and are added to or co-formulated in a therapeutic composition in order to enhance, elicit, and/or modulate the innate, humoral, and/or cell-mediated immune response against the active ingredients.

Use of the compounds in the manufacture of a composition or medicament for treating cancer, brain disorders, infectious disease, and/or inflammatory diseases is also within the ambit of the invention.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the disclosure. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration, and nothing therein should be taken as a limitation upon the overall scope of the invention.

Example 1

Synthesis of β-Carboline Adducts and Dimer Compounds from Tryptamines Using Novel GK Reaction Method This example describes the general reaction procedures for synthesizing β-carboline adducts and various new harmaline dimer compounds using the GK reaction method (see Example 2 below). By varying the length and the particular moiety "$R_1$" of the selected diacid chloride, we can synthesize harmaline dimers with tether length≥3 with substitution at any place of tether. For example, for n=3 and R1=imidazole, the harmaline dimer will be GK506.21m, similarly for n=3 and R1=furan, the harmaline dimer will be GK506.2Fn.

A typical harmaline+aldehyde reaction has a limitation of choosing aldehydes that react with harmaline. This limits the tether length and substitution at the tether. In the case of the GK reaction, we can also synthesize harmaline dimer molecules with extended tether length and multiple substitutions at the tether. The new dimer compounds can have a longer tether length ranging from 3-22 carbons than previous structures, with a wide variety of possible substitutions $R_1$ at one or more than one carbon of the tether, which also differs from previously-possible structures. The harmaline dimers (b) can be achieved from one-pot GK reaction method. Harmine dimers (a) and Tetrahydro harmine dimers (c) can be furnished by treating Harmaline dimers (b) with oxidizing or reducing agents. So, the GK reaction is capable of synthesizing a broader range of harmaline dimers and adducts.

1. General Synthesis of β-Carboline Using Novel GK Reaction Method

Figure 4A:
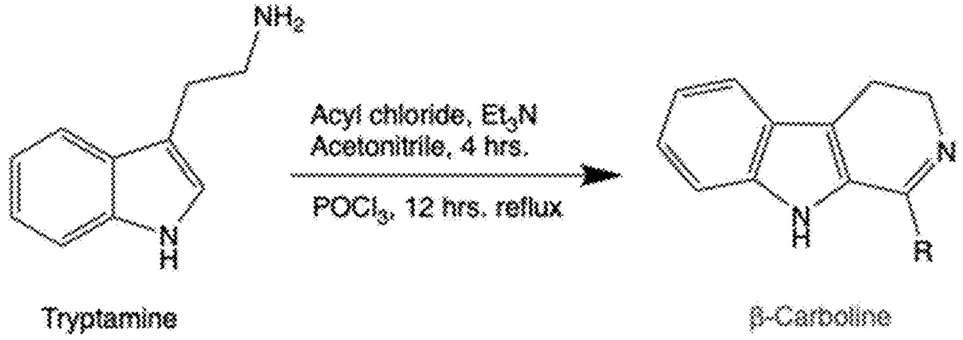
FIG. 4A shows the general reaction scheme for the GK Reaction method used to synthesize β-carboline.

FIG. 4A illustrates the general reaction scheme for using the GK reaction method to synthesize β-carboline.

The novel GK method is a one pot synthesis of β-carboline molecules from tryptamines. As shown in the reaction scheme, acid chloride and tryptamine are added to a flame dried flask containing freshly distilled acetonitrile as the solvent system. Then, dry $Et_3N$ is added, and the resulting solution is refluxed for 4 hours at 90-95° C. After 4 hours, 5-20 eq of $POCl_3$ is added drop wise to the reaction mixture in the same flask containing intermediate (unpurified) reactions products, and the reflux is continued for 12 more hours. After 12 hours, the solution is cooled and then filtered to collect the final product, which will be either β-carboline adducts or dimer compounds depending on whether an acid chloride or diacid chloride is used (and provided adequate tryptamine is to furnish dimers, when desired).

β-Carboline Adducts—General GK Reaction Method

Figure 4B:
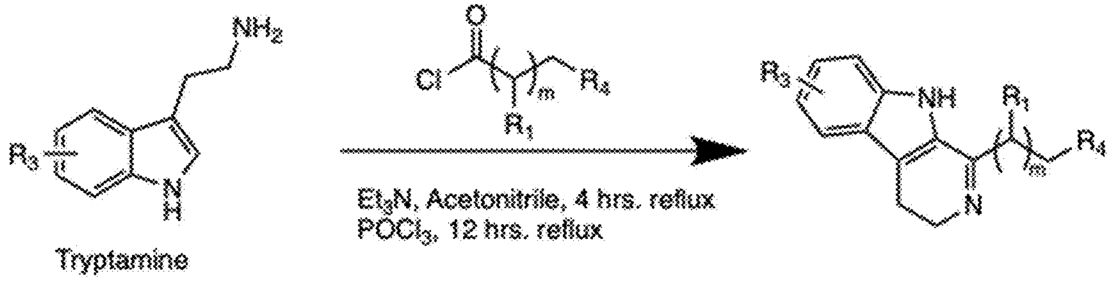
FIG. 4B shows the general reaction scheme for the GK Reaction method used to synthesize β-carboline adducts.

Notably, the GK reaction method can be applied to the synthesis of several β-carboline like molecules by varying the amine and/or acid chloride, as shown is FIG. 4B. Depending on the starting reaction products, the GK method can be used to synthesize a variety of adduct compounds as follows:

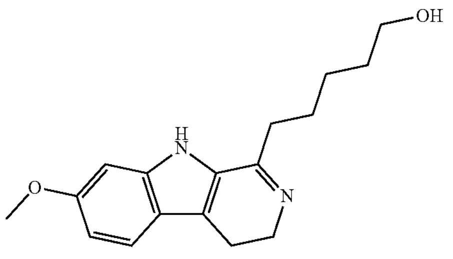

Chemical Formula: $C_{17}H_{22}N_2O_2$
Molecular Weight: 286.38

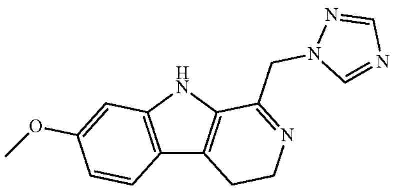

Chemical Formula: $C_{15}H_{15}N_5O$
Molecular Weight: 281.32

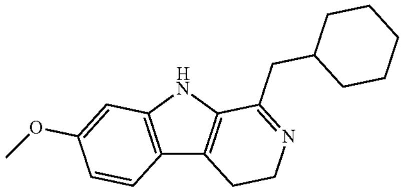

Chemical Formula: $C_{18}H_{23}N_3O$
Molecular Weight: 297.40

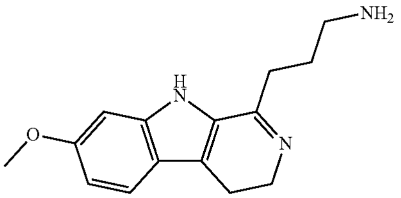

Chemical Formula: $C_{15}H_{19}N_3O$
Molecular Weight: 257.34

-continued

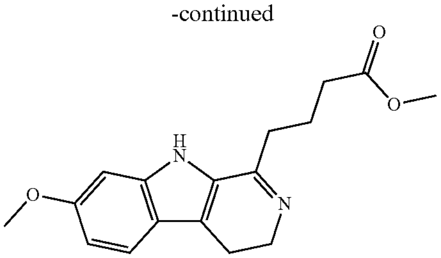

Chemical Formula: $C_{17}H_{20}N_2O_3$
Molecular Weight: 300.36

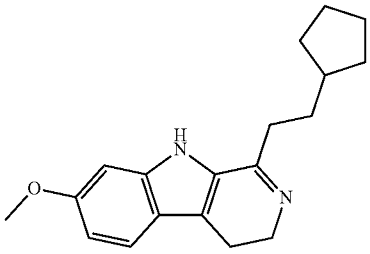

Chemical Formula: $C_{19}H_{24}N_2O$
Exact Mass: 296.19

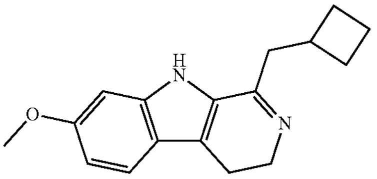

Chemical Formula: $C_{17}H_{20}N_2O$
Exact Mass: 268.16

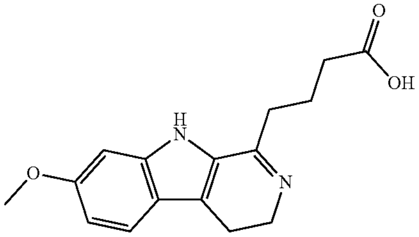

Chemical Formula: $C_{16}H_{18}N_2O_3$
Molecular Weight: 286.33

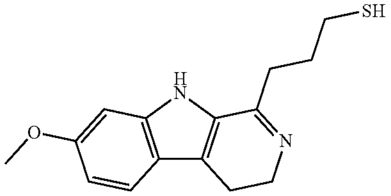

Chemical Formula: $C_{15}H_{18}N_2OS$
Molecular Weight: 274.38

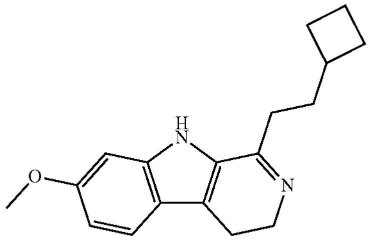

Chemical Formula: $C_{18}H_{22}N_2O$
Exact Mass: 282.17

-continued

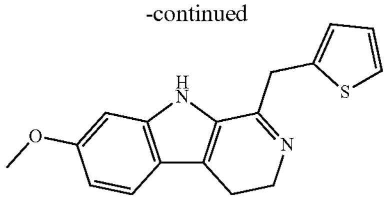

Chemical Formula: $C_{17}H_{16}N_2OS$
Exact Mass: 296.10

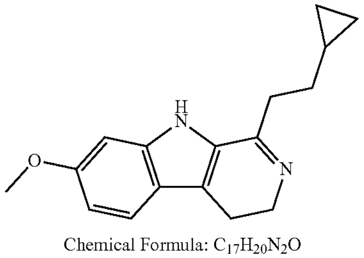

Chemical Formula: $C_{17}H_{20}N_2O$
Exact Mass: 268.16

3. β-Carboline Dimers—General GK Reaction Method

Figure 4C:
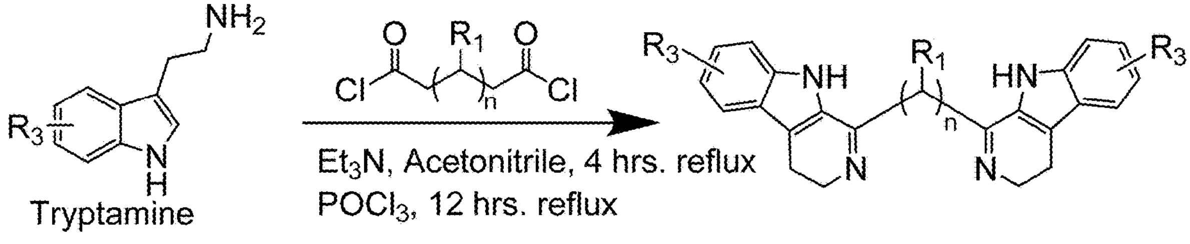
FIG. 4C shows the general reaction scheme for the GK Reaction method used to synthesize β-carboline dimers.

Notably, the GK reaction method can be applied to the synthesis of several β-carboline dimers by varying the amine and/or diacid chloride, as shown in FIG. 4C. Depending on the starting reaction products, the GK method can be used to synthesize a variety of dimer compounds as follows:

a. Synthesis of GZ440/6 Using Novel GK Reaction Method

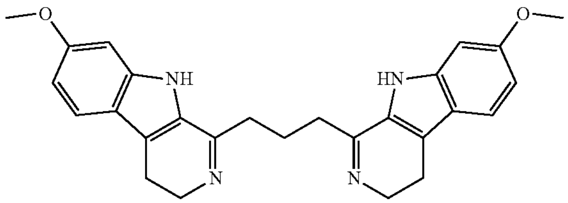

GZ440/6

Figure 5:
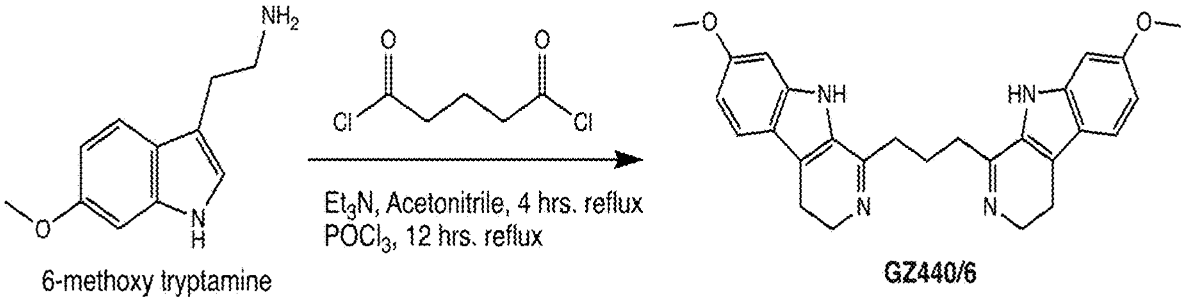
FIG. 5 show the general reaction scheme for the GK Reaction method used to synthesize GZ440/6 dimer.

The reaction scheme for synthesizing GZ440/6 is shown in FIG. 5. As generally shown in the reaction scheme, 300 mg of β-methoxy tryptamine, 2 eq (0.0016 moles), was added to a flame dried flask in glove bag under nitrogen. The flask was equipped with a condenser, and the setup was transferred to a hood. 100 mL of freshly distilled acetonitrile was added to the flask using a glass syringe. Then, 0.22 mL of $Et_3N$, 2 eq (0.0016 moles), was added to the flask followed by 133 μL of glutaryl chloride, 1 eq (0.0008 moles). The resultant solution was heated to reflux at 90-95° C. for 4 hours. After 4 hours, 1.47 mL of $POCl_3$, 20 eq (0.016 moles), was added to the flask slowly using a glass syringe. Notably, white dense fumes formed during the addition of $POCl_3$, and the formation of a greenish yellow colored precipitation was observed in 60 minutes of the reflux. Then, reflux was continued for 12 more hours. After the reaction was completed, the solution was cooled to room temperature. Further cooling was achieved by keeping the flask in an ice bath for 30 minutes. The resulting solid was collected using vacuum filtration and washed with cold ethanol to furnish 290 mg (83.5%) of yellow colored GZ440/6.

If impurities are detected, a solvent system including 5-10% methanol in dichloromethane can be used to perform column purification, and recrystallisation with ethanol can help in removing salts formed during the reaction. 2-5% isopropyl amine can be used to help prevent the reaction of the compound with the acidic nature of silica or dichloromethane during purification.

Figure 6A:
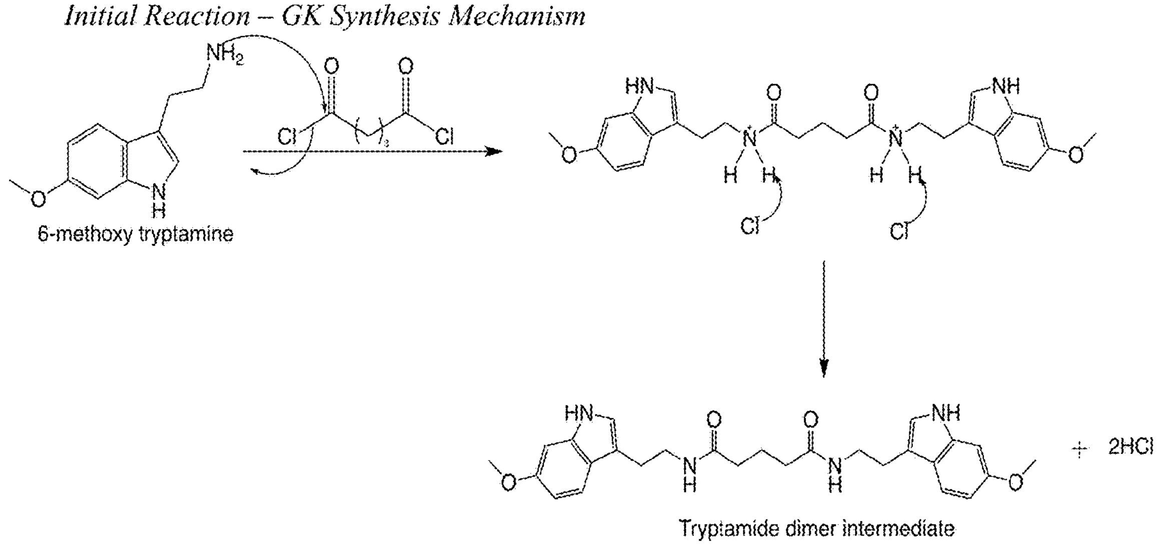
FIG. 6A shows the initial reaction in the GK Reaction methods which forms the tryptamide dimer intermediate.
Figure 6B:
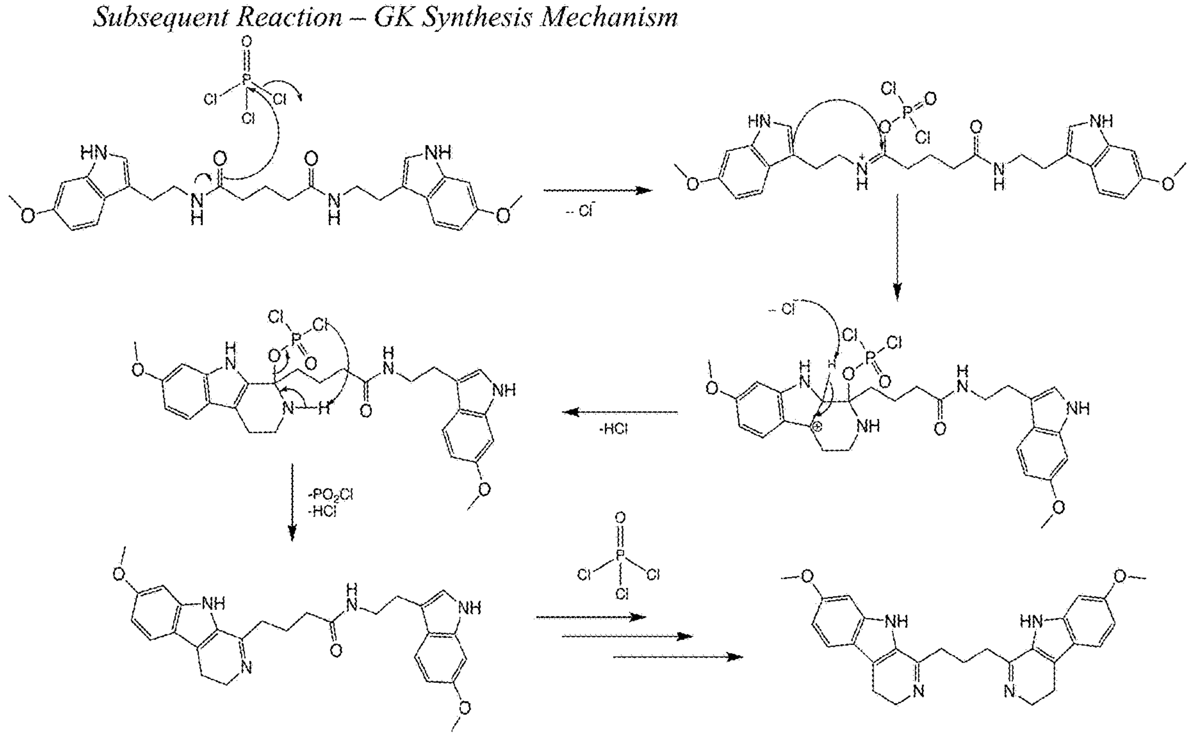
FIG. 6B shoe's the immediately subsequent reaction in which the tryptamide dimer from FIG. 6A reacts with the phosphoryl chloride to yield the final dimer reaction product.

The reaction mechanism of the process is shown in FIG. 6A and FIG. 6B. First, FIG. 6A illustrates the reaction between tryptamine and a diacid chloride to furnish tryptamide dimers (i.e., an $S_N2$ reaction). 2 equivalent of tryptamine reacts with 1 equivalent of diacid chloride furnishes 1 equivalent of tryptamide dimer intermediate and 2 equivalents of HCl byproduct. As shown in FIG. 6B, the resulting tryptamide dimer intermediate then immediately reacts with phosphoryl chloride and to furnish GZ440/6 (i.e., in a Bischler—Napieralski reaction). The second part of the reaction proceeds immediately, without extracting, isolating, or purifying the intermediate tryptamide dimer. The reaction schemes in FIGS. 6A and 6B proceed without interruption in a one-pot synthesis.

Example 2

1. Synthesis of GK282 Adduct

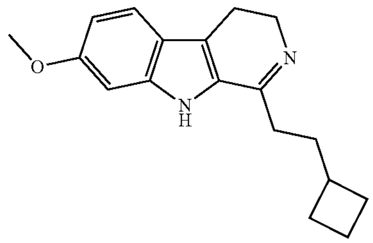

GK282

Chemical Formula: $C_{18}H_{22}N_2O$

Exact Mass: 282.17

Figure 7A:
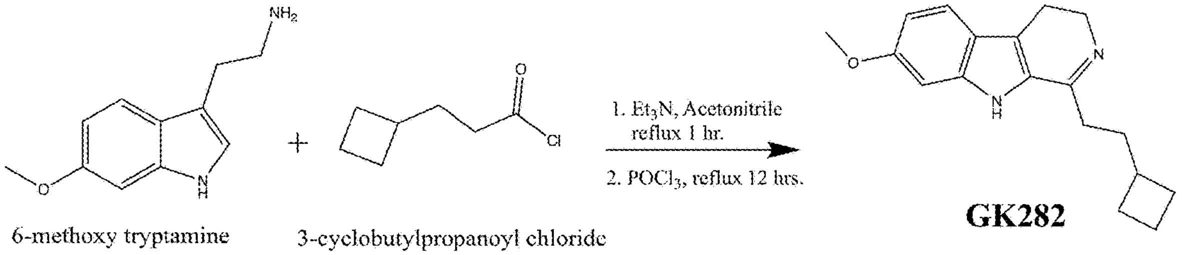
FIG. 7A shows the reaction scheme using the GK Method to synthesize β-carboline adduct GK282.

The reaction scheme for synthesizing this adduct is shown in FIG. 7A. 250 uL of $Et_3N$ was added to flask with 170 uL of 3-cyclobutylpropanoyl chloride in 50 mL of acetonitrile. 340 mg of 6-methoxy tryptamine was added to flask and setup for reflux for 1 hour. After 1 hour, 3.3 mL of $POCl_3$ was added and reflux was continued for 12 more hours. Solution was cooled to room temp. Excess $POCl_3$ and solvent was removed using a simple distillation setup. The resultant pale yellow crude solid was transferred to a clean vial and stored in a freezer. A sample was prepared for LCMS analysis. Gradient solvent system of acetonitrile and water was used with a 10 mins of sample run time. The data confirms the complete conversion of 6-methoxy tryptamine into GK282. ESI(+)MS: m/z [$M+H^+$] calculated for $C_{18}H_{23}N_2O$ 283.18; found 283.17.

2. Attempted Synthesis of Dimer with Short Tether (GK426)

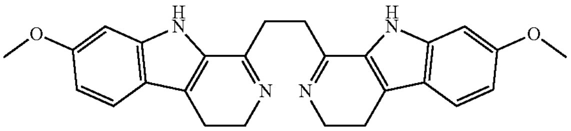

GK426

(Failed compound)

Figure 7B:
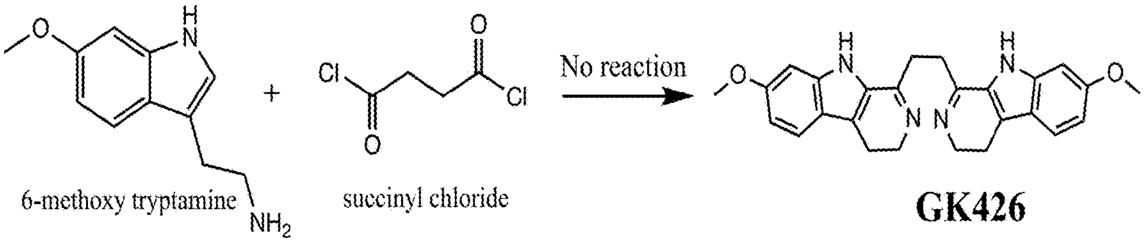
FIG. 7B shows the reaction scheme for the attempted synthesis of β-carboline Dimer GK426 using the GK Method.

The proposed reaction scheme for synthesizing this dimer is shown in FIG. 7B. An attempt to make harmaline dimer with no tether (i.e., linkage of only 2 carbons) was not successful. No desired compound was identified in LCMS analysis. Steric factor could be a reason behind the failure of this reaction, as the tether is not long enough two allow the two tricyclic moieties to be joined.

The invention claimed is:

1. A one-pot method of synthesizing an adduct or dimer compound comprising a β-carboline moiety, the method comprising reacting an indole derivative having a primary amine functionality with a mono acid chloride or a diacid chloride in an acetonitrile solvent system, optionally comprising a neutralizing base, to yield an adduct or dimer intermediate product; and refluxing said intermediate product with a condensation reagent to yield said adduct comprising a β-carboline moiety or a dimer compound comprising two β-carboline moieties, wherein said intermediate product is not isolated or purified from said reaction mixture before said step of adding said condensation reagent, and wherein said reacting and refluxing steps are carried out in the same reaction vessel.

2. The method of claim 1, wherein said indole derivative having a primary amine functionality is an aromatic or heterocyclic primary ethyl amine.

3. The method of claim 1, wherein said indole derivative having a primary amine functionality is tryptamine, 2-pyrrolyl ethylamine, or 2-phenylethylamine.

4. The method of claim 1, wherein said indole derivative having a primary amine functionality is tryptamine.

5. The method of claim 1, wherein said diacid chloride comprises an alkyl chain having four or more carbons.

6. The method of claim 5, wherein said diacid chloride comprises an alkyl chain having five or more carbons and having at least one substitution thereon.

7. The method of claim 1, wherein said diacid chloride is succinyl chloride ($C_4H_4Cl_2O_2$), glutaryl chloride ($C_5H_6Cl_2O_2$), adipoyl dichloride ($C_6H_8Cl_2O_2$), heptanedioyl dichloride ($C_7H_{10}Cl_2O_2$), Octanedioyl dichloride ($C_8H_{12}Cl_2O_2$) nonanedioyl dichloride ($C_9H_{14}Cl_2O_2$), decanedioyl dichloride ($C_{10}H_{16}Cl_2O_2$), undecanedioyl dichloride ($C_{11}H_{18}Cl_2O_2$), dodecanedioyl dichloride tridecanedioyl ($C_{12}H_{20}Cl_2O_2$), dichloride ($C_{13}H_{22}Cl_2O_2$), tetradecanedioyl dichloride ($C_{14}H_{24}Cl_2O_2$), pentadecanedioyl dichloride ($C_{15}H_{26}Cl_2O_2$), hexadecanedioyl dichloride ($C_{16}H_{28}Cl_2O_2$), or docosanedioic acid dichloride ($C_{22}H_{40}Cl_2O_2$).

8. The method of claim 1, wherein said monoacid chloride is acetyl chloride ($C_2H_3ClO$), propionyl chloride ($C_3H_5ClO$), 3-Chloropropionyl chloride ($C_3H_4Cl_{20}$), butyryl chloride ($C_4H_7ClO$), Valeroyl chloride ($C_5H_9ClO$), Isovaleryl chloride ($C_5H_9ClO$), 2-Methylbutyryl chloride ($C_5H_9ClO$), hexanoyl chloride ($C_6H_{11}ClO$), heptanoyl chloride ($C_7H_{13}ClO$), Octonoyl chloride ($C_8H_{15}ClO$), nonanoyl chloride ($C_9H_{17}ClO$), decanoyl chloride ($C_{10}H_{19}ClO$), undecanoyl chloride ($C_{11}H_{21}ClO$), Lauroyl chloride ($C_{12}H_{23}ClO$), tridecanoyl chloride ($C_{13}H_{25}ClO$), tetradecanoyl chloride ($C_{14}H_{27}ClO$), pentadecanoyl chloride ($C_{15}H_{29}ClO$), palmitoyl chloride ($C_{16}H_{31}ClO$), heptadecanoyl chloride ($C_{17}H_{33}ClO$), stearoyl chloride ($C_{18}H_{35}ClO$), nonadecanoyl chloride ($C_{19}H_{37}ClO$), icosanoyl chloride ($C_{20}H_{39}ClO$), or Thiophene-2-acetyl Chloride ($C_6H_5ClOS$).

9. The method of claim 1, wherein said condensation reagent is phosphoryl chloride.

10. The method of claim 1, wherein said dimer comprises said two β-carboline moieties linked by a tether having at least 3 carbons.

11. The method of claim 1, wherein said adduct or dimer is a harmaline adduct or dimer, said method further comprising converting said harmaline adduct or dimer into a harmine or tetrahydroharmine adduct or dimer by contacting said reaction product with reducing or oxidizing agents.

12. The method of claim 1, wherein said adduct is a) harmine, b) harmaline, or c) tetrahydroharmine adduct:

a)

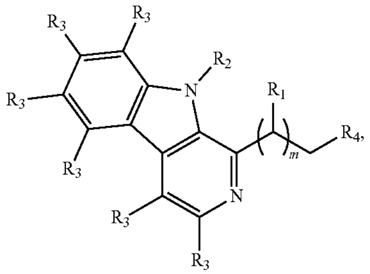

-continued b)

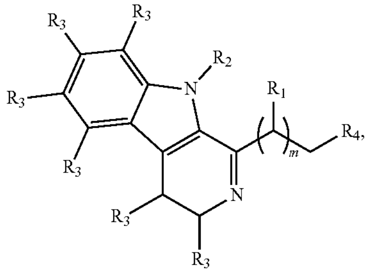

or c)

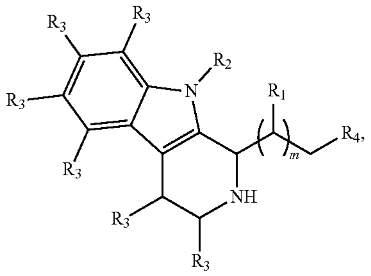

where m is 0-20, and each $R_1$, $R_2$, $R_3$ and $R_4$ is independently selected from the group consisting of:

| Group | |
|---|---|
| $R_1$ | H, halogens, Thiols, alkyls, hydroxy, carboxylic acids, amides, ethers, esters, aldehydes, Aromatic ring with size from 4-10 carbons, Heterocyclic ring with size 4-10 atoms, Aromatic or heterocyclic rings with substitutions, and Fused heterocyclic rings; |
| $R_2$ | H, halogens, Thiols, alkyls, hydroxy, carboxylic acids, amides ethers, esters, aldehydes, Aromatic ring with size from 4-10 carbons, Heterocyclic ring with size 4-10 atoms, substituted aromatic or heterocyclic rings, and Fused heterocyclic rings; |
| $R_3$ | Hydrogen, halogens, sulfonyl chloride, Sulphonic acid, thiols, alkyls, hydroxy, carboxylic acids, amides, ethers, esters, aldehydes, Nitro groups, hydroxy, Alkoxy, Furan, imidazole, Benzene, Pyridine, Indole, Indazole, Cyclooctatetraene, [10]annulene, Pentalene, Indene, Naphthalene, Heptalene, Biphenylene, as-indacene, acenaphthylene, fluorene, phenalene, Anthracene, Pyrene, Fluoranthene, Imidazopyridines, Pyrazopyridines, Oxazolopyridines, Isooxazolopyridines, Cyclopropane, cyclopentane, methyl, ethyl, propyl, isopropyl, pentadiene, hexane, or hexene, any of which may or may not be substituted, and substituted or unsubstituted fused polycyclic and heterocyclic rings; |
| $R_4$ | halogens, Thiols, alkyls, hydroxy, carboxylic acids, amides, ethers, esters, aldehydes, thiazol-2-amine, morpholine, pyrimidine-2,4(1H,3H)-dione, pyrimidine-2,4(1H,3H)-dione, 1-tosyl-1H-pyrrole, 1-chloro-3-(methylsulfonyl)benzene, 4-(thiazol-2-yl)morpholine, pyrimidine-2,4-diamine, Aromatic ring with ring size from 4-10 carbons, Heterocyclic ring with ring size 4-10 atoms, Saturated and unsaturated cyclic hydrocarbon with ring size from 3-10, and fused heterocyclic rings, any of which may or may not be substituted. |

13. The method of claim 1, wherein said dimer is a a) harmine, b) harmaline, or c) tetrahydro harmine dimer:

a)

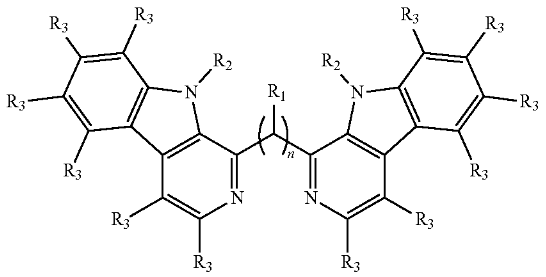

b)

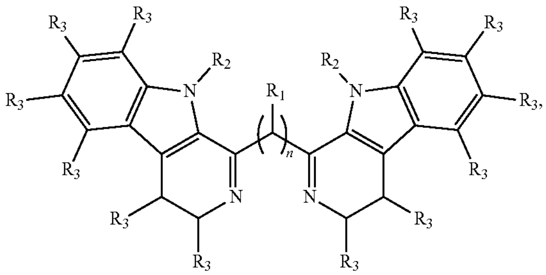

, or

-continued c)

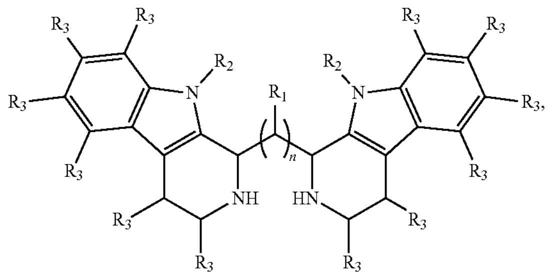

where n is at least 3; and each $R_1$, $R_2$, and $R_3$ is independently selected from the group consisting of:

| Group | |
|---|---|
| $R_1$ | H, halogens, Thiols, alkyls, hydroxy, carboxylic acids, amides, ethers, esters, aldehydes, Aromatic ring with size from 4-10 carbons, Heterocyclic ring with size 4-10 atoms, Aromatic or heterocyclic rings with substitutions, and fused heterocyclic rings; |
| $R_2$ | H, halogens, Thiols, alkyls, hydroxy, carboxylic acids, amides, ethers, esters, aldehydes, Aromatic ring with size from 4-10 carbons, Heterocyclic ring with size 4-10 atoms, Aromatic or heterocyclic rings with substitutions, and fused heterocyclic rings; |
| $R_3$ | H, halogens, Thiols, alkyls, hydroxy, carboxylic acids, amides, ethers, esters, aldehydes, Aromatic ring with size from 4-10 carbons, Heterocyclic ring with size 4-10 atoms, Aromatic or heterocyclic rings with substitutions, and fused heterocyclic rings. |

14. The method of claim 1, wherein said solvent system is free of water or aqueous solvents.

15. The method of claim 1, wherein said final reaction product yield for said adduct comprising a β-carboline moiety or a dimer compound comprising two β-carboline moieties is at least 60% as compared to the starting reactants taken as 100%.

* * * * *